United States Patent
Henglein et al.

(10) Patent No.: US 8,911,546 B2
(45) Date of Patent: Dec. 16, 2014

(54) COSMETIC COMPOSITION FOR THE CREATION OF A COSMETIC COATING HAVING A METALLIC, MULTICOLORED IRIDESCENT APPEARANCE; AND ARTIFICIAL FINGERNAIL

(75) Inventors: Frank Henglein, Nuremberg (DE); Thomas Schuster, Lauf (DE)

(73) Assignee: Eckart GmbH (DE)

(*) Notice: Subject to any disclaimer, the term of this patent is extended or adjusted under 35 U.S.C. 154(b) by 1418 days.

(21) Appl. No.: 10/582,066

(22) PCT Filed: Dec. 9, 2004

(86) PCT No.: PCT/DE2004/002703
§ 371 (c)(1),
(2), (4) Date: Mar. 15, 2007

(87) PCT Pub. No.: WO2005/055965
PCT Pub. Date: Jun. 23, 2005

(65) Prior Publication Data
US 2007/0207099 A1 Sep. 6, 2007

(30) Foreign Application Priority Data
Dec. 10, 2003 (DE) .................... 103 58 091

(51) Int. Cl.
C09C 1/00 (2006.01)
A61Q 1/04 (2006.01)
A61Q 3/02 (2006.01)
A61K 8/26 (2006.01)

(52) U.S. Cl.
CPC .. *A61Q 1/04* (2013.01); *A61Q 3/02* (2013.01); *A61K 8/26* (2013.01)
USPC ............................................ 106/415; 424/63

(58) Field of Classification Search
USPC ............................................ 106/415; 424/63
See application file for complete search history.

(56) References Cited

U.S. PATENT DOCUMENTS 4,321,087 A   3/1982   Levine et al.
5,326,796 A * 7/1994   LeCacheur et al. ............. 524/31

(Continued)

FOREIGN PATENT DOCUMENTS

CH         674 459      6/1990
DE       1 068 864     11/1959

(Continued)

OTHER PUBLICATIONS

Metalure® L-55350 Technical Data Sheet, Eckart Effect Pigments, Revision 5, Edition Jul. 2008.*

(Continued)

*Primary Examiner* — Kaj K Olsen
*Assistant Examiner* — Ross J Christie
(74) *Attorney, Agent, or Firm* — Ostrolenk Faber LLP (57) ABSTRACT

The invention relates to a cosmetic composition for creating a cosmetic coating having a metallic and multicolored iridescent appearance, comprising a liquid phase and a PVD aluminum pigment, wherein said PVD aluminum pigment has diffractive structures containing from approximately 5,000 to approximately 20,000 structural elements per cm and a metallic aluminum content of from 90% to 100% by weight, based on the weight of the aluminum pigment, and is present in the cosmetic composition at a pigmentation level of from 1.0 to 8.0% by weight, based on the total weight of the cosmetic composition. The invention further relates to an artificial fingernail.

17 Claims, 2 Drawing Sheets

(56) References Cited

U.S. PATENT DOCUMENTS

| | | | |
|---|---|---|---|
| 5,624,076 A | | 4/1997 | Miekka et al. ............ 241/3 |
| 5,804,169 A | * | 9/1998 | Ramin ............... 424/61 |
| 5,849,072 A | * | 12/1998 | Sommer et al. ........... 106/403 |
| 6,042,842 A | * | 3/2000 | Lemann et al. ........... 424/401 |
| 6,210,059 B1 | * | 4/2001 | Ramin et al. ............ 424/61 |
| 6,296,839 B1 | * | 10/2001 | Ramin et al. ............ 424/61 |
| 6,333,025 B2 | * | 12/2001 | Ramin ............... 424/61 |
| 6,447,761 B1 | * | 9/2002 | Ramin ............... 424/63 |
| 6,565,835 B1 | | 5/2003 | Socci et al. |
| 2001/0041168 A1 | * | 11/2001 | Ramin ............... 424/61 |
| 2003/0175225 A1 | | 9/2003 | Leacock et al. |
| 2004/0071643 A1 | * | 4/2004 | Vicic et al. ............ 424/61 |
| 2004/0071644 A1 | * | 4/2004 | Mougin et al. ........... 424/61 |
| 2004/0120906 A1 | * | 6/2004 | Toumi et al. ........... 424/61 |
| 2004/0185017 A1 | * | 9/2004 | Mougin et al. ........... 424/61 |
| 2004/0202688 A1 | * | 10/2004 | Mougin et al. ........... 424/401 |
| 2004/0241115 A1 | * | 12/2004 | Ramin ............... 424/61 |
| 2004/0241423 A1 | * | 12/2004 | Ramin et al. ........... 428/323 |
| 2005/0002878 A1 | * | 1/2005 | Lefrancois et al. ........ 424/61 |
| 2005/0100518 A1 | * | 5/2005 | Ilekti et al. ............ 424/61 |
| 2005/0238869 A9 | * | 10/2005 | Ramin et al. ........... 428/323 |

FOREIGN PATENT DOCUMENTS

| | | |
|---|---|---|
| EP | 0 826 745 | 3/1998 |
| EP | 0 826 745 A | 3/1998 |
| JP | 8-502301 | 3/1996 |
| WO | WO 93/23481 | 11/1993 |
| WO | WO 02/03913 | 1/2002 |
| WO | WO 02/03913 A2 | 1/2002 |

OTHER PUBLICATIONS

Metalure® product brochure for nail polish from Eckart GmbH.*
Aluminum pigment dispersions for Nail Polish Metalure®, http://www.eckart.net/markets/cosmetic-personal-care/aluminium-pigment-dispersions-for-nail-polish-metalure.html.*
Metallure® Prismatic product brochure from Eckart GmbH.*
Metalure product brochure entitled "Aluminum Pigment Dispersions for Nail Polish" by Eckart Gmbh (published Mar. 2002).*
Metalure product brochure entitled "Aluminum Pigment Dispersions" by Eckart Gmbh (published Apr. 2005).*
Fragrance Journal, Apr. 2002, pp. 13-18 (with English Abstract).
Translation of Japanese Office Action dated Sep. 30, 2008 in corresponding Application No. 2006-543357.
English translation of the Fragrance Journal article "Development of optical characteristic make-up products", Apr. 2002, pp. 13-18.
XP-002322107: Dr. Joerg Seubert et al., PVD Aluminum Pigments: Superior Brilliance for Coatings & Graphic Arts, pp. 1-9.
Barbara Parker, Advances in Inteference Color, pp. 1-10.
J. Seubert, A Fetz: "PVD Aluminum Pigments: Superior Brilliance for Coatings & Graphic Arts" Jan. 6, 2000, XP002322107.
International Search Report PCT/DE2004/002703 dated Mar. 23, 2005 (European Patent Office).

* cited by examiner

Fig. 1

"Peak to Valley"  "Peak to Peak"  Fig. 2

COSMETIC COMPOSITION FOR THE CREATION OF A COSMETIC COATING HAVING A METALLIC, MULTICOLORED IRIDESCENT APPEARANCE; AND ARTIFICIAL FINGERNAIL

CROSS REFERENCE TO RELATED APPLICATIONS

The present application is a 35 U.S.C. §371 National Phase conversion of PCT/DE2004/002703 filed Dec. 9, 2004, which claims priority of German Application No. 103 58 091.3 filed Dec. 10, 2003. The PCT application was published in the German language.

FIELD OF THE INVENTION

The invention relates to a cosmetic composition for creating a cosmetic coating having a metallic, multicolored iridescent appearance.

BACKGROUND OF THE INVENTION

A nail varnish that lends a metallic appearance to a fingernail is disclosed in WO 02/03913. PVD pigments are used in this nail varnish formulation known in the prior art. Other color effects, in particular a multicolored iridescence, cannot be achieved with this nail varnish.

Pigments are marketed under the trade name SpectraFlair® by Flex Products, Inc. of Santa Rosa, Calif. (USA). The composition and manufacture of these pigments are described in the article "Advances in Interference Color," by Barbara Parker, in the conference proceedings of the Color Cosmetic Summit, Montreal (2003). These pigments are multi-layered effect pigments created by PVD methods having an aluminum core with $MgF_2$ layers deposited thereon. A grating with a defined spacing between grating structures is embossed on these low refracting layers. Each effect pigment produces a prismatic diffraction effect when observed under visible light. This results in a coating showing a rainbow-like effect, provided the effect pigments take on a uniform, plane-parallel orientation within a coated layer on a substrate.

In addition, rainbow effects can also be created with so-called "holographic" effect pigments. The term "holographic" effect pigments includes a plurality of effect pigments showing various structures, such as the so-called "geometric pigments" marketed by Eckart in Fuerth, Germany. In these "geometric pigments," a plurality of polymer layers is deposited on an aluminum core by PVD methods. Said effect pigments have layer thicknesses ranging up to 10 mm and are unsuitable for cosmetic formulations, especially on account of such great layer thicknesses. The aforementioned effect pigments with grating or hologram structures, some of which are already available on the market, all have the considerable disadvantage of being relatively thick effect pigments. This disadvantage severely limits the use of said pigments in cosmetic formulations.

An additional drawback is the fact that the aforementioned effect pigments comprise relatively large particles, ie, particles with diameters greater than 25 μm.

SpectraFlair® pigments, eg, can be used in nail varnishes to produce nail varnish coatings showing a rainbow effect and a metallic appearance. Because of the great layer thickness of approximately 1 mm in SpectraFlair® pigments (Barbara Parker, "Advances in Interference Color" in the proceedings of the Color Cosmetic Summit, Montreal, 2003) and the large particle sizes of from approximately 25 μm to 35 μm, said pigments in a coating do not produce the impression of being a uniform metallic film to the observer; on the contrary, they are perceived by the observer as being individual pigments providing a glittering or sparkling effect.

Such a glittering or sparkling effect, however, is only desirable under certain conditions in cosmetic formulations such as nail varnishes. In this market, most women prefer a nail varnish showing a certain degree of elegance wherein the individual pigment particles are visually perceived as being merged into a smooth metallic film.

Moreover, the rainbow effect should not be too pronounced, as the nail varnish would then look too gaudy.

Consequently, there is a need for cosmetic formulations that provide a coating showing a fine rainbow color effect and having an elegant appearance after they have been applied.

Another disadvantage of the aforementioned effect pigments is their low covering power. The low covering power results from two effects:

On the one hand, all of the aforementioned effect pigments have relatively low contents of aluminum. In said effect pigments, however, only the aluminum core contributes to the covering power, as visible light (wavelengths of 400 to 800 nm) is reflected from only the aluminum core. The lower the proportion of aluminum core in the effect pigment, the more the covering power is reduced. Furthermore, the insufficient covering power of these pigments leads to a low coverage per unit area of the cosmetic coating composition.

On the other hand, the high layer thicknesses of said effect pigments hinder favorable stacking of the pigments in the carrier medium. Geometric pigments with layer thicknesses of 10 mm, for example, are thus completely unsuitable for use in nail varnish, as said pigments are no longer able to orient themselves sufficiently. Good orientation, in particular a substantially plane-parallel alignment to the substrate, such as a fingernail, is required in order to achieve a good visual appearance.

Furthermore, the use of said effect pigments in cosmetic compositions for producing coatings having a metallic appearance and multi-colored iridescence (rainbow effect) is not cost effective due to the very expensive and complicated processes required for their production.

In addition, rainbow effects combined with a highly metallic appearance and luster and having a good covering power can be achieved by using embossed films. For this purpose, metallized synthetic films with a grating structure are used. Such films are produced and marketed, for example, by Kurz GmbH & Co. KG of Fuerth, Germany. Such films, however, cannot be used in cosmetic formulations.

SUMMARY OF THE INVENTION

It is an object of the present invention to prepare a cosmetic composition that, when applied, produces a multi-colored iridescence as well as a lustrous metallic effect giving the impression of being a preferably cohesive metallic layer.

The coverage per unit area of the cosmetic composition with respect to the desired metallic rainbow effect should be as high as possible; ie, the level of pigmentation or the pigment content in the cosmetic formulation should be as low as possible.

The object of the invention is achieved by the preparation of a cosmetic composition for producing a cosmetic coating having a metallic and multi-colored iridescent appearance, said composition including a liquid phase and a PVD aluminum pigment, wherein said PVD aluminum pigment comprises diffraction structures having from about 5,000 to about 20,000 structural elements per cm and a metallic aluminum content of from 90 to 100% by weight, based on the weight of the aluminum pigment, and wherein said PVD aluminum pigment is present in said cosmetic composition to an extent of from 0.05 to 5.0% by weight, based on the total weight of the cosmetic composition.

Preferred developments are given in the subordinate claims.

In addition, the object is achieved by the preparation of an artificial fingernail as claimed. Within the scope of the invention, an artificial fingernail is to be understood as including an artificial toenail.

DETAILED DESCRIPTION OF CERTAIN EMBODIMENTS OF THE INVENTION

The term PVD aluminum pigment implies, within the scope of the invention, that the aluminum pigment has been produced by a PVD process (PVD: physical vapor deposition). Very thin aluminum pigments with an exceptionally smooth, reflective surface can be produced by PVD processes. PVD processes for producing aluminum pigments are known to the person skilled in the art from, for example, EP 0 826 745, which is included herein by reference.

The production of aluminum pigments from aluminum having diffraction structures is described in U.S. Pat. No. 5,624,076. These pigments, also known as embossed pigments, have the major advantage of being composed only of very thin aluminum with a primary layer thickness of from about 25 nm to 60 nm.

The diffraction structures comprise 5,000 to 11,000 grooves per cm according to the teaching of U.S. Pat. No. 5,624,076.

According to the teaching of U.S. Pat. No. 5,624,076, the pigment is produced by embossing a polymer film with a grating structure and then applying aluminum thereto by vapor deposition in a high vacuum. The aluminum is then removed from the polymer film and the resulting foils comminuted to pigments, as is standard practice in the production of metallic effect pigments by PVD methods. A process for producing embossed aluminum pigments is described in U.S. Pat. No. 5,624,076, which is included herein by reference.

Diffraction structures comprising as many as 20,000 diffraction elements per cm can also be produced by this process. Within the scope of the invention, the term "embossed aluminum pigments" is also used below for PVD aluminum pigments comprising diffraction structures.

The diffraction structures are preferably grooves arranged substantially parallel to each other, ie, formed by valleys separated from each other by ridges or peaks. It is obviously also possible to use other diffraction structures on the aluminum pigments. The diffraction structures may, for example, be in the form of concentric groove structures arranged within each other or groove structures arranged in spiral form. It is only essential that the diffraction structures elicit the desired optical effect of a multi-colored iridescence or rainbow color effect to the observer.

The diffraction structures are preferably formed as reflective gratings.

Furthermore, it has been found, surprisingly, that said embossed aluminum pigments are ideally suited for use in cosmetic formulations.

The embossed aluminum pigments are preferably handled in highly diluted dispersions with organic solvents in order to avoid any high degree of agglomeration.

Consequently, the invention relates to a cosmetic composition that, after application, produces a coating comprising a metallic film which is preferably uniform in appearance and has a colored iridescence. The appearance can also be described as a metallic rainbow color effect. Within the scope of the invention, "rainbow color effect" does not imply that a complete separation of visible light into all colors of the spectrum must take place, but rather it is meant that the observer will perceive a multi-colored iridescence in the coating of the invention after it has been applied.

Within the scope of the invention, a cosmetic composition refers to various cosmetic formulations that have a liquid phase, that contain embossed aluminum pigments to be used according to the invention, and that are applied to substantially two-dimensional substrates. The cosmetic preparations are preferably selected from the group consisting of liquid make-up, liquid eye liner, liquid eye shadow, body lotion, perfume, lip gloss, and nail varnish.

According to a preferred embodiment, the cosmetic composition may contain additives and/or supplements that are for example antioxidants, dyes, UV absorbers, emulsifiers, vitamins, odorous substances, medicaments, thixotropic agents and/or extenders.

The cosmetic composition is preferably a nail varnish or a lip gloss formulation.

In the embossed aluminum pigment used in the cosmetic composition of the invention, the metallic, multi-colored appearance or the rainbow color effect appears after said cosmetic composition has been applied to a two-dimensional substrate. The effect is not necessarily discernible in the cosmetic composition per se, as at this point the embossed aluminum pigments are still randomly distributed in the cosmetic composition. An orientation that is preferably plane parallel to the substrate results after the cosmetic composition of the invention has been applied, eg, to natural or artificial fingernails, lips, eyelids, cheeks, or other two-dimensional body surfaces. Said cosmetic composition must comprise a liquid phase in order to enable said orientation of said embossed aluminum pigments. Cosmetic compositions that do not comprise a liquid phase are mostly unsuitable, because a liquid phase is required in order to enable an orientation of the embossed aluminum pigments and thus the desired metallic and multi-colored iridescent effect in the coating after it has been applied.

In other words, to achieve good orientation of the embossed aluminum pigments, a sufficient moisture content in the cosmetic composition is necessary in order to enable an orientation of the effect pigments to take place after the composition has been applied and the solvent has evaporated. Furthermore, the orientation of the embossed aluminum pigments can be improved or enhanced if a mechanical action takes place during the application of the cosmetic composition. This takes place, eg, when a nail varnish is applied with a brush to a natural or an artificial fingernail. When lip gloss is applied to the lips, the orientation is enhanced, eg, by the applicator or roll-on ball of the lip gloss applicator stick. Alternatively, the lip gloss can also be applied to the lips with a brush.

Liquid components that have no detrimental health effects associated with the respective application are preferably used as the liquid phase. In other words, organic solvents may be used in a nail varnish, whereas such solvents can only be used to a limited extent or not at all in a lip gloss. The person skilled in the art, however, will be able to select, without any difficulty, a suitable liquid phase for the respective application, said liquid phase being, for example, an organic solvent, water, oil, gel, or a suitable mixture thereof.

As a rule, a nail varnish composition of the invention consists of components that are non-toxic for this intended use and said composition is suitable for producing a film coating with a metallic rainbow effect on natural or artificial fingernails. The term "non-toxic" as used herein refers in general to the materials listed in EC Directive 76/78.

A nail varnish composition preferably contains a solvent, at least one film-forming component, and an embossed aluminum pigment, wherein said aluminum pigment comprises diffraction structures about having from about 5,000 to about 20,000 structural elements per cm, a layer thickness of from about 20 nm to about 140 nm, preferably from about 20 nm to about 100 nm, and more preferably from about 25 nm to about 80 nm, and has a metallic aluminum content of from 90% to 100% by weight, based on the weight of the aluminum pigment.

The film-forming component preferably contains cellulose nitrate and suitable, non-toxic derivatives thereof, such as cellulose acetate butyrate. The cellulose nitrate preferably has a molecular weight of at least 56,000 g/mol and more preferably at least 112,000 g/mol.

The embossed aluminum pigment is preferably used in the form of a dispersion in an organic solvent for the production of a cosmetic composition. The solids content of the dispersion to be added to a cosmetic composition may therefore comprise from 1% to 15% by weight and preferably from 3% to 10% by weight. With higher concentrations of embossed aluminum pigment, there is the risk that agglomeration of the aluminum pigments will take place.

There is considerable freedom of choice when considering a solvent for a nail varnish composition, as long as the solvents are suitable and approved for this application. Toluene, n-propyl acetate, ethyl acetate, isopropyl alcohol, glycol ether, and n-butyl acetate are examples of solvents that may be used. Ethyl acetate is preferred for nail varnish compositions.

Hexane, heptane, cyclopentane, cyclohexane, cyclic ethers such as tetrahydrofuran or 1,4-dioxane, ethanol, isopropyl acetate, cellosolve acetate, ethyl cellosolve, butyl cellosolve, and mixtures thereof are further examples of organic solvents that may be used in the nail varnish composition.

The solvent content of the nail varnish composition of the invention preferably comprises from 50% to 90% by weight, more preferably from 60% to 85% by weight and even more preferably from 65% to 75% by weight, always based on the total weight of the nail varnish composition.

According to a preferred development of the invention, the nail varnish composition can contain a plasticizer and/or a dispersing agent.

Plasticizers soften, in particular, the binding agent and make it easier to work with. A single plasticizer or a combination of more than one plasticizers may be used. Examples of such plasticizers are: camphor, castor oil, and esters of citric, stearic, oleic, phthalic and benzoic acids.

The phthalates used are preferably dibutyl phthalate, diethyl phthalate, diamyl phthalate, diocytyl phthalate and dibutoxyethyl phthalate, or mixtures thereof. Examples of other plasticizers that may be used are glyceryl triacetate, glyceryl tripropionate, glyceryl tribenzoate, dibutyl tartrate, benzyl benzoate, triphenyl phosphate, butyl acetyl ricinoleate, butyl stearate, triethyl citrate, acetyl tributyl citrate, saccharose acetate isobutyrate, and mixtures thereof are further examples of plasticizers that may be used.

According to another embodiment of the invention, dispersing agents may be added in order to improve the dispersion of the embossed aluminum pigments and any other effect pigments and/or color pigments used. Preferred examples of dispersing agents are montmorillonite clays such as bentonite and, especially, stearalkonium hectorite or stearalkonium bentonite. Polymeric urea, optionally in combination with bentonites, may also be used as a dispersing agent.

Other additives include other effect pigments and/or coloring agents such as color pigments and/or dyes. The effect pigments used may, in particular, be pearl luster pigments. However, it is preferable to add these in relatively low concentrations of about approximately 1% by weight or less in order not to impair the rainbow color effect.

According to a preferred development of the invention, color pigments may also be added. Preferably, the color pigments are likewise added in low concentrations of about approximately 3% by weight or less and more preferably about approximately 1% by weight or less. Examples of suitable color pigments include $TiO_2$, iron oxide (red, black, yellow), chromium oxide for green shades, ultramarine blue, and typical nail varnish pigments used in the cosmetics industry.

Furthermore, the nail varnish composition of the invention may contain further additives such as thixotropic agents, UV absorbers, antioxidants, coloring agents, emulsifiers, vitamins, odorous substances, extenders, or medicaments. Said additives are known in the art and, when added, are used in the standard quantities.

A nail varnish composition of the invention, which is preferably composed of non-toxic components, preferably contains an embossed aluminum pigment consisting of grating-like embossed aluminum comprising from 5,000 to 20,000 grating structures per cm and preferably from 7,000 to 15,000 diffraction structures per cm, having a primary layer thickness of from 20 nm to 140 nm, preferably from about 20 to about 100 nm and more preferably from about 30 nm to about 80 nm, and a metallic aluminum content of from 90% to 100% by weight, based on the total weight of the aluminum pigment, said pigment occurring at a pigmentation level of from 0.05% to a maximum of 5% by weight, based on the total weight of the nail varnish. A pigmentation level of from 0.1% to 2% by weight, based on the total weight of the nail varnish, is more preferable.

It is particularly preferable that the nail varnish composition contains non-toxic components, cellulose nitrate having a molecular weight of at least 56,000 g/mol, solvent, plasticizer, dispersing agent, and embossed aluminum pigment having from 5,000 to 20,000 diffraction structures per cm, preferably from 7,000 to 15,000 diffraction structures per cm, and having a primary layer thickness of from 20 nm to 140 nm, preferably from about 20 nm to about 100 nm and more preferably from about 30 nm to about 80 nm, and a metallic aluminum content of from 90% to 100% by weight, based on the total weight of the aluminum pigment, said pigment being used at a pigmentation level of from 0.05% to 5% by weight, based on the total weight of the nail varnish. A pigmentation level of from 0.1% to 2% by weight, based on the total weight of the nail varnish, is more preferable.

Surprisingly, it has been found that the embossed aluminum pigment present in the cosmetic composition provides very high coverage per unit area in use, ie, has outstanding covering power. Coating compositions containing said embossed aluminum pigment have an exceptionally high covering power. Said embossed aluminum pigment can therefore be advantageously used at very low pigmentation levels in the cosmetic composition of the invention. The embossed aluminum pigment content in said cosmetic composition is from 0.05% to 5.0% by weight and preferably from 0.1% to 2.0% by weight, based on the total weight of the cosmetic composition.

The embossed aluminum pigments have a primary layer thickness of preferably from about 20 nm to 140 nm and consequently they differ considerably in layer thickness from aluminum pigments produced by conventional means such as wet milling, such conventionally produced pigments having thicknesses ranging from about 200 nm to 1,000 nm. Because of their low thickness values, embossed aluminum pigments are so flexible that they fit perfectly to a substrate, ie, they cling closely to the substrate, as it were.

The primary layer thickness refers herein to the actual layer thickness of the aluminum. In the embossed pigments used in the coating compositions of the invention, said layer thickness is preferably from 20 nm to 140 nm, more preferably from 20 nm to 100 nm and even more preferably from 20 nm to 80 nm. Primary layer thicknesses of from 25 nm to 75 nm or from 30 nm to 65 nm are most preferable.

The secondary layer thickness, on the other hand, denotes the distance between the peaks on the opposite sides of an embossed aluminum pigment.

Figure 1:
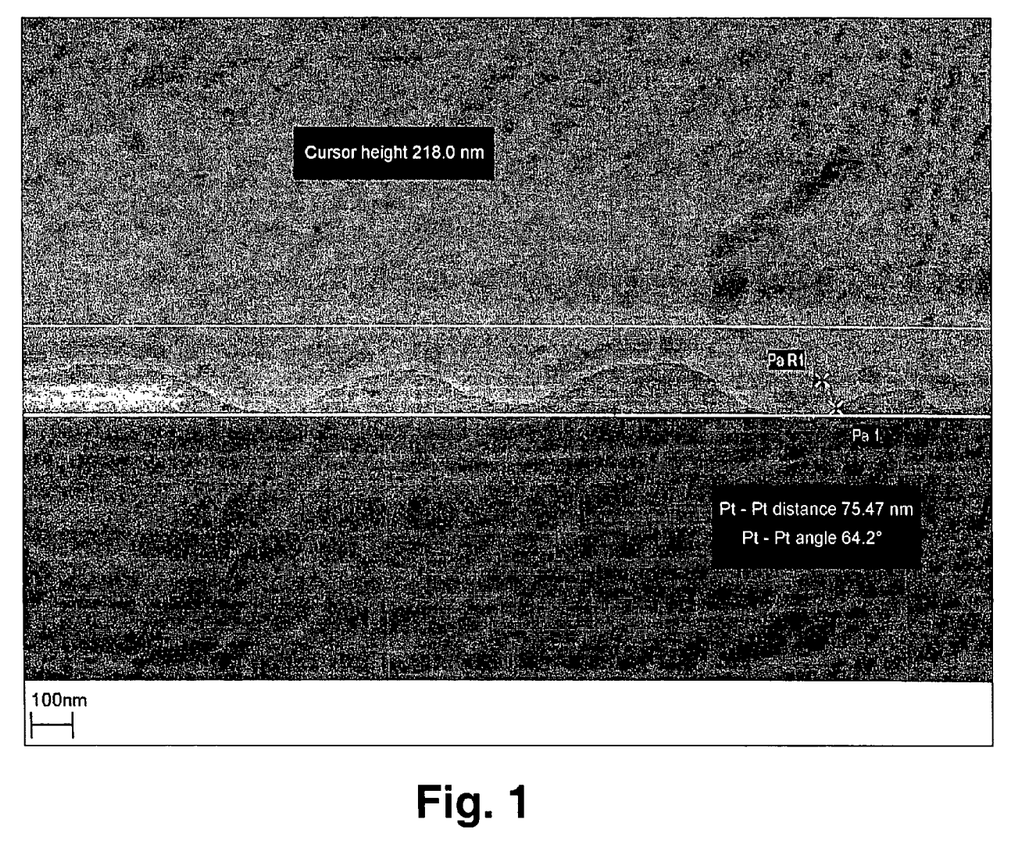
FIG. 1 is a scanning electron microscope (SEM) image of an embossed PVD aluminum pigment.

FIG. 1 shows an SEM image of an embossed PVD aluminum pigment. The diffraction structure of an embossed PVD aluminum pigment at 50,000 times magnification can be discerned in FIG. 1. FIG. 1 illustrates more precisely what is meant in this document by primary layer thickness and secondary layer thickness. The primary layer thickness is the actual thickness of the aluminum pigment between two opposing points on the top and bottom surfaces of the aluminum pigment. In FIG. 1, these are the points PaR1 on the upperside and Pa1 on the underside of the aluminum pigment. The secondary layer thickness is the thickness of the pigment corresponding to the spacing between the white lines drawn along the peaks of the top and bottom surfaces of the pigment, respectively.

The secondary layer thickness of the effect pigments of the coating composition of the invention is preferably from 150 nm to 400 nm, more preferably from 175 nm to 350 nm, very preferably from 200 nm to 300 nm and most preferably from 220 nm to 280 nm.

In principle, the embossed aluminum pigments can assume two extreme positions relative to each other, specifically a "peak to valley" alignment or a "peak to peak" alignment.

Figure 2:
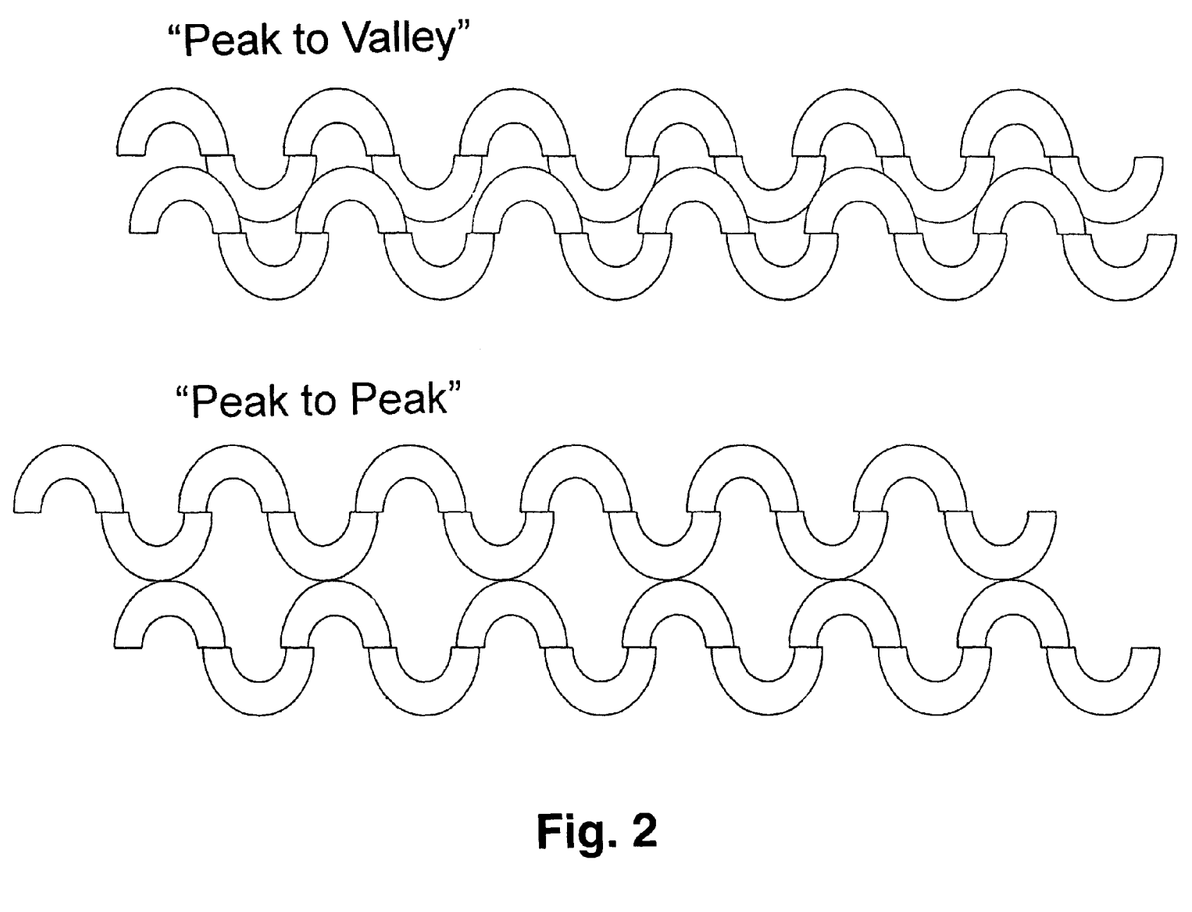
FIG. 2 is a schematic illustration of what is meant by a "peak to valley" and a "peak to peak" alignment, respectively.

FIG. 2 illustrates schematically what is meant by a "peak to valley" and a "peak to peak" alignment, respectively.

The spacing between the embossed aluminum pigments is very small in a "peak to valley" alignment. The contact surfaces and consequently the forces of attraction between the embossed aluminum pigments might be very large in this case.

The spacing between the aluminum pigments is greatest in a "peak to peak" alignment, wherein the contact surfaces or contact points are consequently minimal. The risk of agglomeration is considerably reduced in this alignment of the embossed aluminum pigments.

It has been found in the present invention that the agglomeration tendency in the cosmetic composition, preferably a nail varnish or a lip gloss, is surprisingly low or even non-existent.

The person skilled in the art would expect the aluminum pigments to agglomerate in a medium of increased viscosity, as is indeed the case with smooth, unembossed PVD aluminum pigments, such as Metalure® (marketed by Eckart of Fuerth, Germany).

It is assumed that the embossed aluminum pigments in the cosmetic composition arrange themselves predominantly in a "peak to peak" alignment. In the "peak to peak" alignment, there is sufficient fluid phase, eg, water, organic solvent, oil, wax, etc., and/or dispersing agent disposed between the embossed aluminum pigments to additionally counteract the undesirable agglomeration effect. Furthermore, it is assumed that the embossed aluminum pigments are arranged so that the peak lines are aligned crosswise rather than parallel to one another, which counteracts stacking of said aluminum pigments and consequently agglomeration thereof.

It is this "peak to peak" alignment that is presumably responsible for allowing the possibility of preparing a cosmetic composition which will consistently have a high viscosity despite its content of embossed aluminum pigments. The embossed structure, ie, the diffraction structures, seems to counteract agglomeration of the pigments. This makes it possible to formulate stable cosmetic compositions, especially nail varnish compositions and the lip gloss compositions described below.

The purpose of lip gloss is to give the lips a moist, seductive appearance. Lip gloss compositions contain various kinds of oils and waxes in their broadest sense. The oil component gives the composition a certain fluid consistency, whereas the waxes raise the melting point and provide physical stability. Lip gloss should have a high luster and not spread out on the lips. Furthermore, the color pigments should not bleed out at the edges of the lips. A pleasant skin sensation is also desirable. This implies that the pigments must not agglomerate in the composition, in particular when platelet-like pigments are used.

Typical waxes used in lip gloss compositions are carnauba wax, candelilla wax, ozocerite, ceresine, microcrystalline wax, synthetic waxes such as the glycerin esters of $C_{18}$ to $C_{36}$ fatty acids, and also cetyl alcohol, stearyl alcohol, lanolin, and beeswax. Ozocerite, and beeswax in particular, are examples of waxes that provide stability, and lanolin imparts homogeneity to the composition during the manufacturing process and provides a pleasant skin sensation.

Examples of suitable oils are castor oil, canola oil, lanolin oil, silicon oils, polybutylene, mineral oils, oleyl alcohol, isocetyl alcohol and esters such as isopropyl myristate or decyl oleate, and mixtures thereof. Castor oil is preferred, as it dissolves dyes and also provides a pleasant skin sensation.

Lip gloss compositions showing a metallic effect are less usual. Lips generally have a rough structure with fine cracks. Such structures tend to be emphasized when metallic pigments such as planar aluminum pigments are applied, which ultimately results in a gray, unattractive appearance.

With the lip gloss compositions of the invention, however, there are obtained, surprisingly, interesting iridescent color effects in combination with a metallic appearance. The luster of the compositions is high and the individual components do not separate. Thus the coating on the lips appears to the observer as a substantially cohesive film.

The pigmentation level of the embossed pigments in the lip gloss composition is preferably from 0.2% to 2.0% by weight and more preferably from 0.3% to 1.0% by weight, based on the total weight of the composition.

The embossed aluminum pigments are present as a dilute suspension in an organic solvent. Said solvent is preferably a solvent of the kind suitable for lipstick. The embossed aluminum pigments are preferably present in butyl glycol in a concentration of from 1% to 15% by weight and preferably from 3% to 10% by weight. The desired end concentration of about 0.05% to about 5% by weight, based on the total weight of the cosmetic composition, is obtained when the remaining components are added during manufacture of the cosmetic composition.

According to a preferred embodiment, the lip gloss composition contains additional coloring agents such as colored pigments and/or dyes. Visually attractive effects can be achieved by mixing colored pigments with the embossed aluminum pigments. All colored pigments approved for lipsticks may be used as colored pigments for this purpose.

The embossed aluminum pigments create a metallic luster and iridescent colors in the rainbow spectrum. This color effect is particularly pronounced in direct sunlight. Due to the low thickness of the embossed aluminum pigments and to form factors, ie, the ratios of length to secondary layer thickness, usually in the range of from 60 to 120, the iridescent color effect is clearly visible without the individual particles in the applied lip gloss being clearly visible, and there is consequently no sparkling effect. This lends to the lip gloss an elegant appearance showing smooth multi-colored iridescence.

Based on the primary layer thickness, the form factors are preferably within a range of from 150 to 1000, whilst the size of the embossed aluminum pigments preferably does not substantially exceed 20 μm.

When mixed, color pigments and effect pigments can effectively complement each other. In the proper concentrations, neither pigment overshadows the effect of the other pigment. A lip gloss of this kind no longer appears silvery, but rather it appears as a metallic color with an iridescent color effect.

The color pigments are primarily used in concentrations of from 0.5% to 5.0% by weight and preferably from 1% to 2.5% by weight, based on the total weight of the cosmetic composition. Within these limits, their coloring effect is sufficiently strong without overshadowing the effects produced by the embossed aluminum pigments.

Furthermore, additives such as perfumes, antioxidants, light stabilizing agents, and preserving agents may be present in the lip gloss composition of the invention. Such additives are standard substances known in the art.

EXAMPLES

The following Examples are provided only for purposes of illustration and are not to be construed as limiting the invention in any manner.

I. Nail Varnish Composition

Example 1

| Substance | Concentration in % by weight |
| --- | --- |
| Cellulose nitrate | 15 |
| Ethyl acetate | 21.15 |
| n-Butyl acetate | 39% |
| Isopropyl alcohol | 8% |
| Polyester binding agent | 9% |
| Dibutyl phthalate | 5% |
| Camphor | 1.7% |
| Stearalkonium bentonite | 0.9% |
| Embossed aluminum pigment (based on pigment) | 0.25% |

Preparation

First of all stearalkonium bentonite was dispersed in butyl acetate and activated with a mixture of 2:1 isopropanol/$H_2O$ (30% by weight, based on stearalkonium bentonite). All ingredients, except for the embossed aluminum pigment, were then added and well mixed. Finally the embossed aluminum pigment was added in the form of a 5% by weight dispersion in ethyl acetate with a minimal shearing action by agitation, until a homogeneous dispersion was obtained. The ethyl acetate in the finished nail varnish composition is mainly derived from this dispersion.

Comparative Example 2

| Substance | Concentration in % by weight |
| --- | --- |
| Cellulose nitrate | 15 |
| Ethyl acetate | 19.4 |
| n-Butyl acetate | 36% |
| Isopropyl alcohol | 8% |
| Polyester binding agent | 9% |
| Dibutyl phthalate | 5% |
| Camphor | 1.7% |
| Stearalkonium bentonite | 0.9% |
| Spectraflair ® | 5% |

Herstellung: Analog zu Example 1.

Comparative Example 3

| Substance | Concentration in % by weight |
| --- | --- |
| Cellulose nitrate | 15 |
| Ethyl acetate | 22.4 |
| n-Butyl acetate | 39% |
| Isopropyl alcohol | 8% |
| Polyester binding agent | 9% |
| Dibutyl phthalate | 5% |
| Camphor | 1.7% |
| Stearalkonium bentonite | 0.9% |
| METALURE ® L-55350 (Fa. Eckart) (based on pigment) | 0.1% |

Preparation: Similar to Example 1, except that METALURE® is added in the form of a 10% dispersion in ethyl acetate.

Comparison and Assessment of the Compositions of Examples from 1 to 3:

Optical appearance of Examples 1-3 following application thereof to an artificial fingernail:

| | |
| --- | --- |
| Example 1 of the invention: | glossy silver having slight rainbow effect, coherent metallic coating similar to a "liquid metal". |
| Comparative Example 2: | strong silver gloss having a pronounced rainbow effect, individual particles visible ("sparkling" effect). |
| Comparative Example 3: | lustrous silver without any rainbow effect, coherent metallic coating similar to a "liquid metal". |

The cosmetic compositions according to Example 1 of the invention and Comparative Example 2 had comparable covering powers, as manifested, in both cases, by a pronounced silver gloss following application to artificial fingernails. The same opinion is reached on assessing doctor knife applications of compositions containing varying concentrations of aluminum pigment.

Compared with the composition according to Comparative Example 2 the composition according to Example 1 of the invention required only 1/20 of the amount of aluminum pigment, which is proof of the exceptionally good covering power of the embossed aluminum pigments. Due to the fact that significantly less aluminum pigment is used for the production of the cosmetic composition of the invention, the manufacturing costs thereof are lower.

II. Lip Gloss Composition

Example 4 of the Invention

| Substance | Concentration in % by weight |
|---|---|
| PEG-45/dodecyl glycol copolymer | 5.5% |
| Candelilla wax | 1.0% |
| Hydroxyoctacosanyl hydroxystearate | 9.9% |
| Microcrystalline wax | 5.6% |
| Isopropyl lanolate | 5% |
| Castor oil | 48% |
| Butylene glycol | 22.5% |
| Embossed aluminum pigment | 2.5% |

The first six components of the aforementioned composition according to Example 4 of the invention were mixed with a mixer operated at a low shear rate. The mixture was then heated to a temperature of 80° to 84° C., and an embossed aluminum pigment in the form of a 10% strength suspension in propylene glycol was added until a homogeneous composition was obtained. The molten mixture was then passed through a 3-roller mill, reheated and poured into a predefined mold, where it was allowed to cool to ambient temperature.

The preparation of the composition according to the following Example 5 of the invention or according to the compositions according to the following Comparative Examples 6 to 9 was carried out in a similar manner to that described for Example 4 of the invention.

Example 5 of the Invention

| Substance | Concentration in % by weight |
|---|---|
| PEG-45/dodecyl glycol copolymer | 7.0% |
| Candelilla wax | 1.5% |
| Hydroxyoctacosanyl hydroxystearate | 10.9% |
| Microcrystalline wax | 6.3% |
| Isopropyl lanolate | 7% |
| Castor oil | 54.5% |
| Butylene glycol | 9% |
| Red color pigment Rot Cosmetic D&C Red No. 7 C19-011 (supplied by Sun Chemical Corp.. USA) | 2.9% |
| Embossed aluminum pigment | 0.9% |

Comparative Example 6

| Substance | Concentration in % by weight |
|---|---|
| PEG-45/dodecyl glycol copolymer | 5.5% |
| Candelilla wax | 1.0% |
| Hydroxyoctacosanylhydroxystearate | 9.9% |
| Microcrystalline wax | 5.6% |
| Isopropyl lanolate | 5% |
| Castor oil | 63.1% |
| Butylene glycol | 9.0% |
| Metalure L 55350 (based on pigment) | 0.9% |

Comparative Example 7

| Substance | Concentration in % by weight |
|---|---|
| PEG-45/dodecyl glycol copolymer | 5.5% |
| Candelilla wax | 1.0% |
| Hydroxyoctacosanyl hydroxystearate | 9.9% |
| Microcrystalline wax | 5.6% |
| Isopropyl lanolate | 5% |
| Castor oil | 60.2% |
| Butylene glycol | 9% |
| Red colorigment Red Cosmetic D&C Red No. 7 C19-011 (supplied by Sun Chemical. USA) | 2.9% |
| Metalure L 55350 (based on Pigment) | 0.9% |

Comparative Example 8

| Substance | Concentration in % by weight |
|---|---|
| PEG-45/dodecyl glycol copolymer | 5.5% |
| Candelilla wax | 1.0% |
| Hydroxyoctacosanyl hydroxystearate | 9.9% |
| Microcrystalline wax | 5.6% |
| Isopropyl lanolate | 5% |
| Castor oil | 68% |
| Spectraflair ® | 5.0% |

Comparative Example 9

| Substance | Concentration in % by weight |
|---|---|
| PEG-45/dodecyl glycol copolymer | 7.0% |
| Candelilla wax | 1.5% |
| Hydroxyoctacosanyl hydroxystearate | 10.9% |
| Microcrystalline wax | 6.3% |
| Isopropyl lanolate | 7% |
| Castor oil | 59.4% |
| Red color pigment Red Cosmetic D&C Red No. 7 C19-011 (supplied by Sun Chemical) | 2.9% |
| Spectraflair ® | 5% |

Comparison and Assessment of the Compositions of Examples 4 to 9:

The results of the comparison and the assessment are summarized in Table 1.

TABLE 1

Results for lip gloss

| Sample | Appearance of lip gloss composition | Appearance following application of lip gloss |
|---|---|---|
| Example 4 (invention) | Homogenous, no agglomeration | Silver metallic, iridescent colors particularly in sunlight; no individual particles visible, optically coherent film |

TABLE 1-continued

Results for lip gloss

| Sample | Appearance of lip gloss composition | Appearance following application of lip gloss |
|---|---|---|
| Example 5 (invention) | Homogenous, no agglomeration | Red metallic, iridescent colors particularly in sunlight; no individual particles visible, optically coherent film |
| Comparative Example 6 | Homogenous, agglomeration | Gray; no iridescent colors; not even in sunlight |
| Comparative Example 7 | Homogenous, agglomeration | Gray; with weak reddish color, no iridescent colors; not even in sunlight |
| Comparative Example 8 | Homogenous, no agglomeration | Silver metallic, iridescent colors particularly in sunlight; individual particles visible (sparkle effect), no coherent film |
| Comparative Example 9 | Homogenous, no agglomeration | Reddish metallic, iridescent colors particularly in sunlight; individual particles visible (sparkle effect), no coherent film |

What is claimed is:

1. A nail varnish having a metallic and multicolored iridescent appearance, said nail varnish comprising a liquid phase, at least one film-forming component, a PVD aluminum pigment and at least one of a plasticizer and a dispersing agent, wherein said PVD aluminum pigment has diffractive structures containing from approximately 5,000 to approximately 20,000 structural elements per cm and a metallic aluminum content of from 90 to 100% by weight, based on the weight of the aluminum pigment, and is present in the nail varnish at a pigmentation level of from 0.05 to 5.0% by weight, based on the total weight of the nail varnish, wherein the nail varnish also comprises a solvent in an amount of from 50% to 90% by weight, based on the total weight of the nail varnish, and with the proviso that the nail varnish does not include pearl luster pigments, and wherein, upon evaporation of said solvent, the pigment is oriented essentially plane parallel to a substrate to which said nail varnish has been applied.

2. The nail varnish as defined in claim 1, characterized in that said aluminum pigment has from approximately 7,000 to approximately 15,000 structural elements per cm.

3. The nail varnish as defined in claim 1, characterized in that said film forming component comprises cellulose nitrate having a molecular weight of more than 56,000 g/mol.

4. The nail varnish as defined in claim 1, characterized in that said film-forming component comprises cellulose nitrate.

5. The nail varnish as defined in claim 1, characterized in that said film-forming component comprises cellulose acetate butyrate having a molecular weight of more than 83,000 g/mol.

6. The nail varnish as defined in claim 1, characterized in that said liquid phase is an organic solvent.

7. The nail varnish as defined in claim 1, characterized in that said nail varnish contains, as plasticizer, at least dibutyl phthalate, optionally together with saccharose acetate isobutyrate.

8. The nail varnish as defined in claim 1, characterized in that said nail varnish contains, as dispersing agent, at least one of bentonites and polymeric urea.

9. The nail varnish as defined in claim 1, characterized in that the aluminum pigment is present at a pigmentation level of from 0.1% to 2.0% by weight.

10. The nail varnish as defined in claim 1, characterized in that said nail varnish additionally contains at least one coloring agent.

11. The nail varnish as defined in claim 10, characterized in that said coloring agent is at least one of a colored pigment and a dye.

12. The nail varnish as defined in claim 1, characterized in that said diffractive structures are a reflection grating.

13. The nail varnish as defined in claim 1, characterized in that said PVD aluminum pigment has a layer thickness of from approximately 20 nm to approximately 140 nm.

14. An artificial fingernail, characterized in that said artificial fingernail is coated with a nail varnish as defined in claim 1.

15. The nail varnish as defined in claim 6, wherein said organic solvent is selected from the group consisting of toluene, n-propyl acetate, isopropyl acetate, isopropyl alcohol, ethyl acetate, ethanol, glycol ether, n-butyl acetate, methyl proposol acetate, and mixtures thereof.

16. The nail varnish as defined in claim 1, wherein the solvent content is from 50% to 85% by weight, based on the total weight of the nail varnish.

17. The nail varnish as defined in claim 1, wherein the solvent content is from 50% to 75% by weight, based on the total weight of the nail varnish.

* * * * *